United States Patent
Yamaguchi et al.

(10) Patent No.: US 6,303,796 B1
(45) Date of Patent: Oct. 16, 2001

(54) β-DIKETONE COMPOUNDS β-DIKETONE COMPOUNDS COORDINATED TO METAL, METHOD OF ORGANIC SYNTHESIS WITH THESE, AND CATALYST

(75) Inventors: Masahiko Yamaguchi; Masayuki Sato, both of Miyagi (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/623,100
(22) PCT Filed: Feb. 24, 1999
(86) PCT No.: PCT/JP99/00857
§ 371 Date: Feb. 20, 2001
§ 102(e) Date: Feb. 20, 2001
(87) PCT Pub. No.: WO99/43668
PCT Pub. Date: Sep. 2, 1999

(30) Foreign Application Priority Data

Feb. 26, 1998 (JP) .................................... 10-062204

(51) Int. Cl.[7] .................. C07D 311/96; C07D 319/06
(52) U.S. Cl. ............................ 549/274; 549/285
(58) Field of Search ..................... 549/274, 285

(56) References Cited

PUBLICATIONS

Sato et al, Tetrahedron, 47(30), pp., 5689–5708, 1991.*
Marciano et al, J. Am. Chem. Soc., 112(20), pp. 7320–7328, 1990.*

* cited by examiner

*Primary Examiner*—Ba K. Trinh
(74) *Attorney, Agent, or Firm*—Sughrue, Mion, Zinn, Macpeak & Seas, PLLC

(57) ABSTRACT

The present invention provides a novel β-diketone compound represented by formula (3):

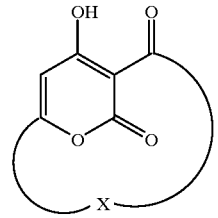

(3)

[wherein X represents $(CH_2)_n$; n represents an integer of 2–20; and the $CH_2$ of X may be replaced by an oxygen atom, a hetero ring, or an aromatic ring, but oxygen atoms are not sequentially arranged in X], and a metal-coordinated β-diketone compound in which a metal is coordinated with the β-diketone compound. The compound of the present invention can be easily synthesized, and serves as a catalyst for asymmetric synthesis which can provide high asymmetric yield and chemical yield.

7 Claims, No Drawings

β-DIKETONE COMPOUNDS β-DIKETONE COMPOUNDS COORDINATED TO METAL, METHOD OF ORGANIC SYNTHESIS WITH THESE, AND CATALYST

This application is a 371 of PCT/JP99/00857 dated Feb. 24, 1999.

TECHNICAL FIELD

The present invention relates to a novel organic compound which can be employed as a catalyst in an organic synthesis reaction, particularly in an asymmetric synthesis reaction, an optical resolution reaction, or an asymmetric recognition reaction.

BACKGROUND ART

Methods for synthesizing an optically active form of a chiral compound are roughly classified into the following three methods: (1) method in which an optically active compound is employed as a starting raw material; (2) method in which a racemic mixture is optically resolved; and (3) asymmetric synthesis method using an asymmetric catalyst.

In the method (2), a target compound is resolved as a diastereomer from a racemic mixture after formation of a salt by use of an optically active carboxylic acid or amine, or after esterification or amidation by use of an optically active carboxylic acid. Amines or carboxylic acids derived from natural products may be employed as a resolution reagent, but employment of such a reagent results in a low optical resolution yield of a racemic mixture. Therefore, in order to obtain a wider range of target compounds, a novel resolution agent must be provided.

In the method (3), a large quantity of optically active compounds can be synthesized by use of a catalytic amount of another optically active compound, and thus the method is most economical and effective. Enzymes derived from organisms or chemically synthesized catalysts may be employed as a catalyst for asymmetric synthesis. Of these, enzymes derived from organisms are chemically unstable and have disadvantageously high substrate specificity, and thus such enzymes are not generally employed. Meanwhile, few asymmetric catalysts are available that are easily synthesized and have high asymmetric yield and chemical yield, although a variety of chemically synthesized asymmetrical catalysts are available.

In view of the foregoing, an object of the present invention is to provide a compound which is easily synthesized and serves as an optical resolution agent that can attain a high optical resolution percentage, and a compound which is easily synthesized and serves as an asymmetric synthesis catalyst that can attain high asymmetric yield and chemical yield.

DISCLOSURE OF THE INVENTION

The present inventors have conducted extensive studies on a useful and novel optically active compound. As a result, the inventors have found that a particular β-diketone compound can serve as an optical resolution agent, and that a metal-coordinated β-diketone compound which is obtained by coordinating a particular β-diketone compound with a metal is effective as an asymmetric synthesis catalyst. The present invention has been accomplished on the basis of these findings.

Accordingly, a first aspect of the present invention is to provide a precursor of a β-diketone compound represented by the following formula (2):

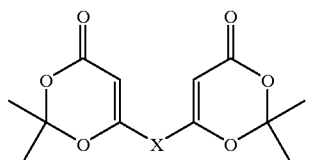

(2)

[wherein X represents $(CH_2)_n$; n is an integer of 2–20; and the $CH_2$ of X may be replaced by an oxygen atom, a hetero ring, or an aromatic ring, but oxygen atoms are not sequentially arranged in X].

A second aspect of the present invention is to provide a β-diketone compound represented by the following formula (3):

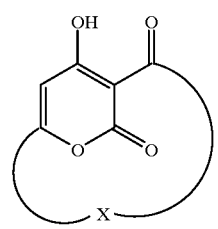

(3)

[wherein X represents $(CH_2)_n$; n is an integer of 2–20; and the $CH_2$ of X may be replaced by an oxygen atom, a hetero ring, or an aromatic ring, but oxygen atoms are not sequentially arranged in X].

A third aspect of the present invention is to provide an optically active enantiomeric β-diketone compound represented by the following formula (3):

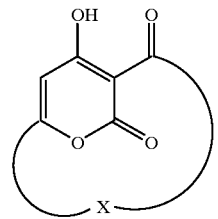

(3)

[wherein X represents $(CH_2)_n$; n is an integer of 7–11; and the $CH_2$ of X may be replaced by an oxygen atom, a hetero ring, or an aromatic ring, but oxygen atoms are not sequentially arranged in X].

A fourth aspect of the present invention is to provide an optical resolution agent comprising the β-diketone compound of the third aspect.

A fifth aspect of the present invention is to provide a metal-coordinated β-diketone compound in which a metal is coordinated with the β-diketone compound of the second or third aspect.

A sixth aspect of the present invention is to provide an organic synthesis method characterized in that a metal-coordinated β-diketone compound is prepared by coordinating a metal with the β-diketone compound of the second or third aspect, and the resultant metal-coordinated β-diketone compound is employed as a catalyst for an organic synthesis reaction, an asymmetric synthesis reaction, or an asymmetric recognition reaction.

A seventh aspect of the present invention is to provide a catalyst for an organic synthesis reaction, an asymmetric synthesis reaction, or an asymmetric recognition reaction, characterized by comprising the metal-coordinated β-diketone compound of the fifth aspect.

BEST MODE FOR CARRYING OUT THE INVENTION

The present invention will next be described in detail.

The compound of the present invention represented by the aforementioned formula (2) may be obtained by heating the β-diketone compound represented by the below-described formula (1) in toluene.

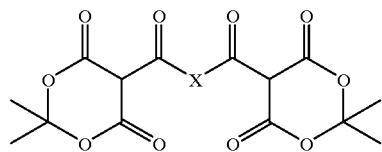

(1)

In this case, the β-diketone compound represented by the above formula (1) may be obtained, for example, through condensation between a dicarboxylic acid dichloride represented by the following formula (4) and Meldrum's acid represented by the following formula (5) in the presence of pyridine:

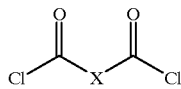

(4)

[wherein X represents $(CH_2)_n$; n is an integer of 2–20; and the $CH_2$ of X may be replaced by an oxygen atom, a hetero ring, or an aromatic ring, but oxygen atoms are not sequentially arranged in X].

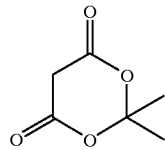

(5)

The β-diketone compound of the present invention represented by the aforementioned formula (3) may be obtained at a high yield by heating the compound of the present invention represented by the aforementioned formula (2) at a very low concentration in boiling xylene or chlorobenzene.

In each of the formulas representing the compounds of the present invention, X is preferably $(CH_2)_n$. However, in consideration of the reaction mechanism, X may be any atomic groups that are thermally stable and do not react with ketene, such as o-, m-, or p-substituted benzene derivatives, naphthalene compounds, hetero rings, and ethers formed of ethylene glycol units. Therefore, in the formulas, X represents $(CH_2)_n$, n is an integer of 2–20, and the $CH_2$ of X may he replaced by an oxygen atom, a hetero ring, or an aromatic ring, but oxygen atoms are not sequentially arranged in X.

In accordance with the type or size of X of the β-diketone compound of the present invention represented by the formula (3), plane asymmetry may be generated due to the restricted rotation of a pyrrone ring, and the compound may be resolved into optically active enantiomers. Optical resolution of the compound is carried out by use of an optically active tertiary amine such as quinine, quinidine, cinchonine, cinchonidine, or sparteine. Alternatively, the compound may be reacted with an optically active primary amine to form enamine diastereomers, the diastereomers may be separated from each other through fractional recrystallization or column chromatography, and then each of the separated diastereomers may be hydrolyzed to remove an amine, to thereby obtain optically active enantiomers.

The compound of the present invention represented by the formula (3) is not limited to an optically active form, and functions as a bidentate ligand like acetylacetone. The compound may react with a variety of metals to form a complex, i.e., a metal-coordinated β-diketone compound, and the β-diketone compound may be employed as a catalyst for organic synthesis reactions. In addition, it is known that the β-diketone compound is useful as an intermediate for other large cyclic compounds, since a pyrrone ring of the compound may be opened or replaced by other rings (D. A. Barton and W. D. Ollis, Comprehensive Organic Chemistry, Vol. 4, Heterocyclic Compounds, Ed. by P. G. Sammes, Pergamon Press Ltd., Oxford, 1979, pp. 644–658).

In the metal-coordinated β-diketone compound of the present invention, metals which may be employed are not particularly limited, so long as they can be coordinated with the compound. Examples of such metals include titanium, zirconium, hafnium, copper, ytterbium, and europium.

In the metal-coordinated β-diketone compound of the present invention, the number of the β-diketone compounds which coordinate with a metal is 1 through 4. In addition, in accordance with a suitable coordination number of a metal employed, a halogen, a hydrogen atom, or a hydroxyl group is coordinated with the metal after coordination of two of the β-diketone compounds.

The metal-coordinated β-diketone compound of the present invention has, for example, a structure represented by the following formula (6):

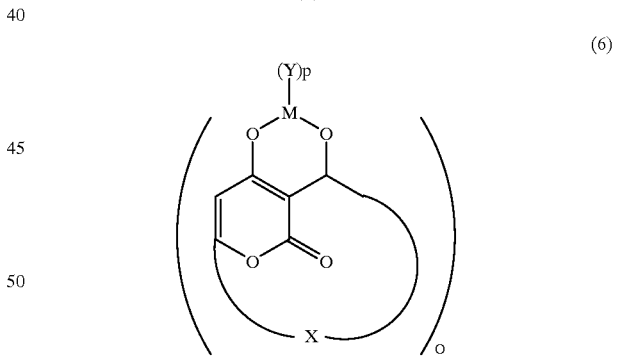

(6)

[wherein M represents a metal; X represents $(CH_2)_n$; Y represents a halogen atom, a hydrogen atom, or a hydroxyl group; n is an integer of 2–20; o is an integer of 1–4; p is an integer of 0–6; and the $CH_2$ of X may be replaced by an oxygen atom, a hetero ring, or an aromatic ring, but oxygen atoms are not sequentially arranged in X]. The metal-coordinated β-diketone compound may comprise a bond between the metal and another oxygen atom of the β-diketone compound, or may be a complex formed of a plurality of metals and a plurality of the β-diketone compounds. In the metal-coordinated β-diketone compound, each of the bonds may be a covalent bond or a coordinate bond.

The metal-coordinated β-diketone compound may take the form of a mixture so long as the compound satisfies the above-described conditions. For example, such a mixture includes a mixture of a compound in which one of the β-diketone compounds is coordinated with a metal and a compound in which two of the β-diketone compounds are coordinated with a metal.

When being limited to an optically active form, the compound of the present invention represented by the formula (3) has a cyclophane structure, and thus the molecular structure is firmly fixed. In addition, a plane of the compound is sterically blocked to a significant degree due to the presence of X (cross-linking chain) of the formula. Analogous compounds are described in "N. Kanomata, T. Nakata, Angew. Chem. Int. Ed. Engl., 1997, 36, 1207."

Therefore, the compound can provide high asymmetry in the vicinity of a metal with which the compound is coordinated, and can be effectively employed in an asymmetric synthesis reaction, an asymmetric recognition reaction, and applied reactions thereof, as an optically active ligand unlike other acetylacetone compounds.

EXAMPLES

The present invention will next be described in more detail by way of examples, which should not be construed as limiting the invention thereto.

Examples 1 through 9
<Synthesis of a Compound Represented by Formula (1)>

Meldrum's acid (0.10 mol) and pyridine (0.250 mol) were dissolved in dichloromethane (200 ml), and the resultant solution was cooled with ice. A dicarboxylic acid dichloride represented by the aforementioned formula (4) (0.050 mol) in dichloromethane (50 ml) was added dropwise to the solution over 15 minutes while the solution was stirred. The resultant mixture was stirred for another 30 minutes while being cooled with ice. Subsequently, the mixture was stirred at room temperature for two hours. To the resultant reaction mixture, 10 w/w% hydrochloric acid (100 ml) was added, to thereby make the solution acidic. Thereafter, dichloromethane was removed from the solution under reduced pressure at room temperature. Crystals were obtained through suction filtration, and washed with water and then dried. The resultant crystals were recrystallized from a solvent mixture of dichloromethane and ether (1:5), to thereby yield colorless prisms of the aforementioned formula (1).

The resultant compound was subjected to identification through ultimate analysis and by use of IR spectra, $^1$H-NMR spectra, and $^{13}$C-NMR spectra. Also, the melting point was determined.

The results obtained in respective Examples are shown in Tables 1 and 2.

TABLE 1

| | X in formula (1) | Yield | Melting point (° C.) | Ultimate analysis Found (Calculated) |
|---|---|---|---|---|
| Ex. 1 | $(CH_2)_6$ | 76% | 94–98 | C: 56.33 (56.22) H: 6.37 (6.15) |
| Ex. 2 | $(CH_2)_7$ | 88% | 87–88 | C: 57.09 (57.25) H: 6.46 (6.41) |
| Ex. 3 | $(CH_2)_8$ | 74% | 88–89 | |
| Ex. 4 | $(CH_2)_9$ | 74% | 79–80 | C: 59.09 (58.95) H: 6.97 (6.89) |

TABLE 1-continued

| | X in formula (1) | Yield | Melting point (° C.) | Ultimate analysis Found (Calculated) |
|---|---|---|---|---|
| Ex. 5 | $(CH_2)_{10}$ | 75% | 90–91 | |
| Ex. 6 | $(CH_2)_{11}$ | 71% | 78–79 | C: 60.74 (60.46) H: 7.42 (7.31) |
| Ex. 7 | $(CH_2)_{12}$ | 70% | 89–91 | |
| Ex. 8 | $(CH_2)_{16}$ | 87% | 96–98 | C: 63.78 (63.57) H: 8.31 (8.19) |
| Ex. 9 | $(CH_2)_{18}$ | 83% | 100–102 | C: 64.10 (64.61) H: 8.34 (8.48) |

TABLE 2

$^1$H-NMR(400MHz, CDCl$_3$)δ

| Example 1 | 1.47(4H, m), 1.67(4H, m), 1.74(12H, s), 3.07(4H, t, J=7.7Hz), 15.30(2H, s) |
|---|---|
| Example 2 | 1.40(6H, m), 1.68(4H, m), 1.74(12H, s), 3.07(4H, t, J=7.5Hz), 15.30(2H, s) |
| Example 4 | 1.28–1.42(12H, m), 1.70(2H, q, J=7.7Hz), 1.74(12H, s), 3.06(4H, t, J=7.7Hz), 15.30(2H, s) |
| Example 6 | 1.22–1.42(12H, m), 1.70(6H, q, J=7.7Hz), 1.74(12H, s), 3.06(4H, t, J=8.0Hz), 15.29(2H, s) |
| Example 8 | 1.22–1.42(24H, m), 1.70(4H, q, J=7.7Hz), 1.73(12H, brs), 3.06(4H, t, J=7.5Hz), 15.28(2H, s) |
| Example 9 | 1.20–1.36(24H, m), 1.70(4H, q, J=7.7Hz), 1.73(12H, s), 3.06(4H, t, J=7.5Hz), 15.28(2H, s) |

Examples 10 through 19
<Synthesis of a Compound Represented by Formula (2)>

A compound represented by formula (1) (0.025 mol) and anhydrous acetone (0.050mol) were dissolved in toluene (80 ml), and the resultant solution was heated under reflux for one hour. The resultant reaction mixture was subjected to silica gel column chromatography with a solvent mixture of hexane and ethyl acetate (3:1), to thereby yield a compound represented by the aforementioned formula (2).

The resultant compound was subjected to identification through ultimate analysis and by use of IR spectra, $^1$H-NMR spectra, and $^{13}$C-NMR spectra. Also, the melting point was determined.

The results obtained in respective Examples are shown in Tables 3 and 4.

TABLE 3

| | X in formula (2) | Yield | Melting point (° C.) | Ultimate analysis Found (Calculated) |
|---|---|---|---|---|
| Ex. 10 | $(CH_2)_6$ | 80% | 54–55 | C: 63.98 (63.91) H: 7.70 (7.69) |
| Ex. 11 | $(CH_2)_7$ | 89% | 31–32 | C: 64.66 (64.74) H: 8.10 (8.01) |
| Ex. 12 | $(CH_2)_8$ | 76% | 42–46 | C: 65.62 (65.57) H: 8.19 (8.20) |
| Ex. 13 | $(CH_2)_9$ | 75% | Oily product | C: 66.10 (66.28) H: 8.43 (8.48) |
| Ex. 14 | $(CH_2)_{10}$ | 80% | 25–26 | C: 66.82 (66.97) H: 8.65 (8.69) |
| Ex. 15 | $(CH_2)_{11}$ | 73% | Oily product | C: 67.48 (67.91) H: 8.98 (8.89) |
| Ex. 16 | $(CH_2)_{12}$ | 76% | 28–29 | C: 68.11 (68.25) H: 8.95 (9.00) |
| Ex. 17 | $(CH_2)_{16}$ | 55% | 54–55 | C: 70.27 (70.29) H: 9.81 (9.62) |
| Ex. 18 | $(CH_2)_{18}$ | 84% | 62–63 | C: 71.09 (71.15) H: 9.89 (9.88) |

TABLE 3-continued

| | X in formula (2) | Yield | Melting point (° C.) | Ultimate analysis Found (Calculated) |
|---|---|---|---|---|
| Ex. 19 | $(CH_2)_4$—(o-Ph)—$(CH_2)_4$ | 40% | Oily product | C: 70.85 (70.55) H: 7.80 (7.75) | o-Ph: o-phenylene group

TABLE 4

| | $^1$H-NMR(400MHz, CDCl$_3$)δ |
|---|---|
| Example 10 | 1.36(4H, m), 1.56(4H, m), 1.68(12H, s), 2.22(4H, t, J=7.5Hz), 5.23(2H, s) |
| Example 11 | 1.34(6H, m), 1.55(4H, m), 1.68(12H, s), 2.22(4H, t, J=7.3Hz), 5.23(2H, s) |
| Example 12 | 1.31(8H, m), 1.54(4H, m), 1.68(12H, s), 2.21(4H, t, J=7.5Hz), 5.23(2H, s) |
| Example 13 | 1.30(10H, m), 1.54(4H, m), 1.68(12H, s), 2.21(4H, t, J=7.5Hz), 5.23(2H, s) |
| Example 14 | 1.28(12H, m), 1.54(4H, m), 1.68(12H, s), 2.21(4H, t, J=7.5Hz), 5.23(2H, s) |
| Example 15 | 1.27(14H, m), 1.54(4H, m), 1.68(12H, s), 2.21(4H, t, J=7.3Hz), 5.23(2H, s) |
| Example 16 | 1.27(16H, m), 1.54(4H, m), 1.68(12H, s), 2.21(4H, t, J=7.3Hz), 5.23(2H, s) |
| Example 17 | 1.26(24H, m), 1.53(4H, m), 1.68(12H, s), 2.21(4H, t, J=7.9Hz), 5.23(2H, s) |
| Example 18 | 1.26(28H, m), 1.54(4H, m), 1.68(12H, s), 2.21(4H, t, J=7.3Hz), 5.23(2H, s) |
| Example 19 | 1.61–1.66(8H, m), 1.67(12H, m), 2.26(4H, t, J=6.8Hz), 2.62(4H, t, J=7.2Hz), 5.23(2H, s), 7.10–7.16(4H, m) |

Examples 20 through 28
<Synthesis of a Racemic Mixture of a Compound Represented by Formula (3)>

Anhydrous chlorobenzene (250 ml) was heated under reflux in a 500-ml flask equipped with an air-cooling tube (diameter: about 2.5 cm, length: 40 cm) while moisture was excluded. The compound represented by the aforementioned formula (2) (1.0 mmol) in anhydrous chlorobenzene (10 ml) was added dropwise to the flask through a microsyringe by use of a syringe pump over 20 hours. The solution of the compound represented by formula (2) was added dropwise directly to the chlorobenzene surface in the flask. After completion of addition, the resultant mixture was heated under reflux for another 30 minutes, and then the solvent was removed under reduced pressure, to thereby obtain an oily product. The oily product was further distilled under reduced pressure, to thereby yield a racemic mixture of a compound of formula (3) in the form of a colorless oily product or crystals.

The resultant racemic mixture was subjected to identification through ultimate analysis and by use of IR spectra, $^1$H-NMR spectra, and $^{13}$C-NMR spectra. Also, the melting point was determined.

The results obtained in respective Examples are shown in Tables 5 and 6.

TABLE 5

| | X in formula (3) | Yield | Melting point (° C) | Ultimate analysis Found (Calculated) |
|---|---|---|---|---|
| Ex. 20 | $(CH_2)_7$ | 89% | 99–100 | C: 66.02 (66.10) H: 6.81 (6.78) |
| Ex. 21 | $(CH_2)_8$ | 76% | Oily product | C: 66.91 (67.17) H: 7.34 (7.25) |
| Ex. 22 | $(CH_2)_9$ | 75% | 92–93 | C: 68.18 (68.18) H: 7.61 (7.58) |
| Ex. 23 | $(CH_2)_{10}$ | 80% | 73–75 | C: 68.81 (69.06) H: 7.97 (7.91) |
| Ex. 24 | $(CH_2)_{11}$ | 73% | 77–78 | C: 69.85 (69.86) H: 8.22 (8.22) |
| Ex. 25 | $(CH_2)_{12}$ | 76% | 62–65 | C: 70.15 (70.54) H: 8.52 (8.56) |
| Ex. 26 | $(CH_2)_{16}$ | 55% | Oily product | C: 72.85 (72.93) H: 9.40 (9.39) |
| Ex. 27 | $(CH_2)_{18}$ | 84% | Oily product | C: 73.75 (73.85) H: 9.60 (9.74) |
| Ex. 28 | $(CH_2)_4$—(o-Ph)—$(CH_2)_4$ | 44% | 95–96 | C: 71.09 (71.15) H: 9.89 (9.88) |

TABLE 6

| | $^1$H-NMR(400MHz, CDCl$_3$)δ |
|---|---|
| Example 20 | 0.18(1H, m), 1.20(6H, m), 1.55(1H, m), 2.01(2H, m), 2.35(1H, m), 2.53(1H, m), 2.62(1H, m), 3.63(2H, m), 6.05(1H, s), 13.60(1H, brs) |
| Example 21 | 0.81(1H, m), 1.02(2H, m), 1.13(4H, m), 1.34(2H, m), 1.61(1H, m), 2.34(1H, m), 2.68(1H, m), 3.59(1H, m), 6.03(1H, s), 14.11(1H, brs) |
| Example 22 | 0.68(1H, m), 0.81(2H, m), 1.13(4H, m), 1.40(8H, m), 2.01(2H, m), 2.34(1H, m), 2.53(2H, m), 3.62(1H, m), 6.03(1H, s), 14.89(1H, s) |
| Example 23 | 1.08(10H, m), 1.36(1H, m), 1.52(1H, m), 1.76(4H, m), 2.34(2H, m), 2.67(1H, m), 4.00(1H, m), 5.99(1H, m), 16.02(1H, s) |
| Example 24 | 1.00(4H, m), 1.25(10H, m), 1.61(2H, m), 1.89(2H, m), 2.31(2H, m), 2.70(1H, m), 3.87(1H, m), 5.97(1H, s), 16.32(1H, s) |
| Example 25 | 1.00–1.40(18H, m), 1.76(4H, m), 2.50(2H, m), 5.97(1H, s), 16.84(1H, s) |
| Example 26 | 1.20–1.35(22H, m), 1.34(2H, m), 1.69(4H, m), 3.05(2H, t, J=7.2Hz), 5.93(1H, s), 16.99(1H, s) |
| Example 27 | 1.21–1.35(26H, m), 1.40(2H, m), 1.69(4H, m), 2.53(2H, t, J=7.2Hz), 5.93(1H, s), 16.99(1H, s) |
| Example 28 | 1.07(1H, m), 1.38–1.60(3H, m), 1.73–2.10(5H, m), 2.17–2.61(5H, m), 2.85(1H, ddd), 3.86(1H, ddd), 5.98(1H, s), 7.09(4H, m), 15.46(1H, s) |

Examples 29 through 38
<Synthesis of an Optically Active Imine Represented by Formula (3)>

A racemic mixture of a compound represented by the aforementioned formula (3) (5.0 mmol) and optically active (R)-1-phenylamine (5.0 mmol) was dissolved in benzene (30 ml), and the resultant solution was heated under reflux for one hour. The resultant reaction mixture was subjected to silica gel column chromatography with a solvent mixture of hexane and ethyl acetate (5:1), to thereby yield an imine form of an (R)-optically active compound (represented by formula (3)), i.e., an (R, R) imine form of the compound, and then an (S) imine form of the compound, i.e., an (S, R) imine form of the compound.

The resultant imine form was subjected to identification through ultimate analysis and by use of IR spectra, $^1$H-NMR spectra, and $^{13}$C-NMR spectra. Also, the melting point was determined.

The results obtained in respective Examples are shown in Tables 7 and 8.

TABLE 7

| | Steric Relation | X in formula (3) | Melting point (° C.) | (c1, CHCl$_3$) |
|---|---|---|---|---|
| Ex. 29 | (R, R) | (CH$_2$)$_7$ | 161–162 | [a]D$^{24}$ = −34.1 |
| Ex. 30 | (R, R) | (CH$_2$)$_8$ | 176–178 | [a]D$^{20}$ = −0.42 |
| Ex. 31 | (R, R) | (CH$_2$)$_9$ | 100–101 | [a]D$^{22}$ = −27.3 |
| Ex. 32 | (R, R) | (CH$_2$)$_{10}$ | 119–120 | [a]D$^{22}$ = −53.1 |
| Ex. 33 | (R, R) | (CH$_2$)$_4$—(o-Ph)—(CH$_2$)$_4$ | Oily product | [a]D$^{24}$ = −26.6 |
| Ex. 34 | (S, R) | (CH$_2$)$_7$ | 144–145 | [a]D$^{22}$ = −80.2 |
| Ex. 35 | (S, R) | (CH$_2$)$_8$ | 125–126 | [a]D$^{22}$ = −102.0 |
| Ex. 36 | (S, R) | (CH$_2$)$_9$ | 172–173 | [a]D$^{22}$ = −95.2 |
| Ex. 37 | (S, R) | (CH$_2$)$_{10}$ | 110–112 | [a]D$^{21}$ = −110.3 |
| Ex. 38 | (S, R) | (CH$_2$)$_4$—(o-Ph)—(CH$_2$)$_4$ | 174–175 | [a]D$^{24}$ = −48.4 |

TABLE 8

$^1$H-NMR(400MHz, CDCl$_3$)δ

| | |
|---|---|
| Example 29 | 0.90(1H, m), 1.07(1H, m), 1.21(1H, m), 1.45(5H, m), 1.64(3H, d, J=6.8Hz), 1.92(2H, m), 2.44(3H, m), 3.66(1H, m), 4.76(1H, q, J=6.7Hz), 5.79(1H, s), 7.31(5H, m), 11.96(1H, brs) |
| Example 30 | 1.07(1H, m), 1.10–1.40(8H, m), 1.50–1.90(6H, m), 2.27(1H, m), 2.43(1H, m), 2.55(1H, m), 3.71(1H, m), 4.87(1H, q, J=6.7Hz), 5.79(1H, s), 7.32(5H, m), 12.59(1H, brs) |
| Example 31 | 0.80–1.60(14H, m), 1.68(3H, d, J=6.8Hz), 2.36(1H, m), 2.45(2H, m), 3.51(1H, brs), 4.91(1H, q, J=7.2Hz), 5.79(1H, s), 7.28(5H, m), 13.70(1H, brs) |
| Example 32 | 1.20(12H, m), 1.47(1H, m), 1.60–1.69(5H, m), 1.81(1H, m), 2.19(1H, m), 2.43(1H, m), 2.59(2H, m), 4.19(1H, brs), 4.96(1H, q, J=7.2Hz), 5.76(1H, s), 7.38(5H, m), 14.10(1H, brs) |
| Example 33 | 0.88(1H, m), 1.40(4H, m), 1.63(3H, d), 1.65–2.11(5H, m), 2.27(1H, m), 2.42–2.58(3H, m), 2.71(1H, m), 3.71(1H, m), 4.90(1H, q, J=7.0Hz), 5.72(1H, s), 7.05–7.13(4H, m), 7.23–7.41(5H, m), 13.77(1H, s) |
| Example 34 | 0.47(1H, m), 0.75(2H, m), 1.20–1.50(6H, m), 1.60(3H, m), 1.87(1H, m), 2.41(2H, m), 2.58(1H, m), 3.75(1H, m), 4.91(1H, q, J=6.8Hz), 5.79(1H, s), 7.34(5H, m), 12.09(1H, brs) |
| Example 35 | 0.75(2H, m), 1.00–1.40(7H, m), 1.55–1.70(6H, m), 2.25(1H, m), 2.56(2H, m), 3.78(1H, m), 4.98(1H, q, J=7.5Hz), 5.79(1H, s), 7.29(5H, m), 12.67(1H, brs) |
| Example 36 | 0.54(2H, m), 0.80–1.60(10H, m), 1.68(3H, d, J=6.8Hz), 1.88(2H, m), 2.35(1H, m), 2.43(1H, m), 2.60(1H, m), 3.64(1H, brs), 4.98(1H, q, J=7.3Hz), 5.77(1H, s), 7.30(5H, m), 13.76(1H, brs) |
| Example 37 | 0.88(1H, m), 0.90–1.40(12H, m), 1.45(1H, m), 1.50–1.67(5H, m), 1.77(1H, m), 2.18(1H, m), 2.59(2H, m), 4.31(1H, brs), 5.04(1H, q, J=6.8Hz), 5.76(1H, s), 7.38(5H, m), 14.20(1H, brs) |
| Example 38 | 0.70(1H, m), 0.83(1H, m), 1.28(2H, m), 1.45(1H, m), 1.60(3H, d, J=7.0Hz), 1.66(1H, m), 2.23(3H, m), 2.45(1H, m), 2.71(1H, m), 3.83(1H, m), 5.00(1H, q, J=7.0Hz), 5.72(1H, s), 7.16(8H, m), 13.81(1H, s) |

Examples 39 through 46
<Synthesis of an Optically Active Form Represented by Formula (3)>

Potassium hydroxide (22.4 mg, 4.0 mmol) in water (4 ml) was added to an optically active imine form of a compound represented by the aforementioned formula (3) (1.0 mmol) in tetrahydrofuran (5 ml), and the resultant mixture was stirred at room temperature for 20 hours. To the resultant reaction mixture, a 10 w/w% hydrochloric acid aqueous solution (2 ml) was added, to thereby make the solution acidic. Thereafter, the solution was subjected to extraction using ether. The resultant organic layer was washed with salt water, and then dried over anhydrous magnesium sulfate. Subsequently, the solvent was removed, and the resultant residue was recrystallized from pentane (or purified through silica gel column chromatography with a solvent mixture of hexane and ethyl acetate (10:1) when the residue was an oily product), to thereby yield an optically active form ((R) or (S) form) of a compound represented by formula (3).

The resultant optically active form was subjected to identification through ultimate analysis and by use of IR spectra, $^1$H-NMR spectra, and $^{13}$C-NMR spectra. Also, the melting point was determined.

The results obtained in respective Examples are shown in Table 9.

TABLE 9

| | Steric Relation | X in formula (3) | Melting point (° C.) | (c1, CHCl$_3$) |
|---|---|---|---|---|
| Ex. 39 | (R) | (CH$_2$)$_7$ | 81–84 | [a]D$^{26}$ = −290.9 |
| Ex. 40 | (S) | (CH$_2$)$_7$ | 74–76 | [a]D$^{24}$ = +281.1 |
| Ex. 41 | (R) | (CH$_2$)$_8$ | 74–75 | [a]D$^{22}$ = −250.6 |
| Ex. 42 | (S) | (CH$_2$)$_8$ | 75–76 | [a]D$^{22}$ = +252.2 |
| Ex. 43 | (R) | (CH$_2$)$_9$ | Oily product | [a]D$^{24}$ = −194.2 |
| Ex. 44 | (S) | (CH$_2$)$_9$ | Oily product | [a]D$^{24}$ = −186.6 |
| Ex. 45 | (R) | (CH$_2$)$_{10}$ | 62–64 | [a]D$^{23}$ = −95.1 |
| Ex. 46 | (S) | (CH$_2$)$_{10}$ | 63–64 | [a]D$^{22}$ = +95.1 |

Example 47
<Optical Resolution by use of an Optically Active Form of a β-diketone Compound Represented by Formula (3)>

(D1)-1-phenylethylamine (121 mg, 1.0 mmol) and the compound of Example 45 shown in Table 9 (278 mg, 1.0 mmol) were added to benzene, and the resultant mixture was heated under reflux for 30 minutes. After removal of the solvent, the resultant residue was purified through silica gel column chromatography with a solvent mixture of hexane and ethyl acetate (3:1), to thereby yield a low polar (R, R) imine form of the compound of Example 45 shown in Table 9 and a high polar (R, S) imine form of the compound of Example 45 shown in Table 9. Each of the imine forms was subjected to alkali treatment utilizing a customary method. The resultant reaction mixture was subjected to extraction with ether, and the ether layer was washed with salt water, and then dried over anhydrous potassium carbonate. After removal of ether, the resultant residue was distilled, to thereby yield 1-phenylethylamine. Specifically, (R)-1-phenylethylamine ([α]$^{20}$D+29.2 (c4, EtOH)) having a boiling point of 180–185° C. was obtained from the (R, R) imine form at a resolution yield of 92.6% and at an optical purity of 100%. (S)-1-phenylethylamine ([α]$_D$$^{20}$−30.1 (c4, EtOH)) was obtained from the (R, S) amino form at a resolution yield of 86.4% and at an optical purity of 100%.

Example 48
<Asymmetric Catalytic Reaction by use of a Metal-coordinated β-diketone Compound in which Titanium is Coordinated with an Optically Active Form of a β-diketone Compound Represented by Formula (3)>

The compound of Example 45 shown in Table 9 (14 mg, 0.05 mmol) was added to titanium tetrachloride (9.5 mg, 0.05 mmol) in toluene (1.0 ml), and the resultant mixture was stirred until the mixture became uniform. After titanium was coordinated with the compound, the solvent was removed through evaporation under reduced pressure at room temperature. The resultant residue was dissolved in anhydrous tetrahydrofliran (10 ml), and the solution was cooled to −20° C. Separately, benzaldehyde (106 mg, 1.0 mmol) and 1-ethoxy-1-trimethylsiloxyethene (192 mg, 1.2 mmol) were dissolved in anhydrous tetrahydrofuran (2 ml), and the resultant solution was added to the above solution, and then the resultant mixture was stirred at −20° C. for one day. Tetrahydrofuran (2 ml) containing trifluoroacetic acid in an amount of 10 w/w% was added to the resultant reaction mixture, and the mixture was returned to room temperature. The reaction mixture was diluted with water, and then subjected to extraction with ether. The organic layer was washed with salt water, and dried over anhydrous magnesium sulfate. After removal of the solvent, the resultant oily product was purified through silica gel chromatography, to thereby yield colorless oily ethyl (S)-3-hydroxy-3-phenylpropionate ($[\alpha]_D^{20}$−25.5 (cl, $CHCl_3$)) at a yield of 70%.

INDUSTRIAL APPLICABILITY

The present invention provides a novel optically active β-diketone compound, and a novel optically active compound which is derived from the β-diketone compound and can be employed as an optical resolution agent. A metal-coordinated β-diketone compound in which a metal is coordinated with the β-diketone compound is useful as an asymmetric catalyst.

What is claimed is:

1. A precursor of a β-diketone compound represented by the following formula (2):

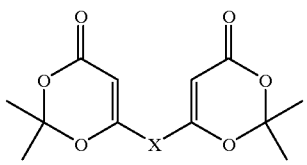

(2)

[wherein X represents $(CH_2)_n$; n is an integer of 2–20; and the $CH_2$ of X may be replaced by an oxygen atom, a hetero ring, or an aromatic ring, but oxygen atoms are not sequentially arranged in X].

2. A β-diketone compound represented by the following formula (3):

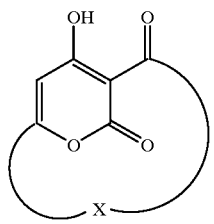

(3)

[wherein X represents $(CH_2)_n$; n is an integer of 2–20; and the $CH_2$ of X may be replaced by an oxygen atom, a hetero ring, or an aromatic ring, but oxygen atoms are not sequentially arranged in X].

3. An optically active enantiomeric β-diketone compound represented by the following formula (3):

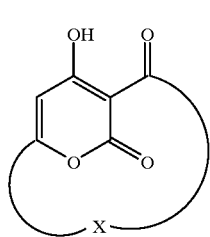

(3)

[wherein X represents $(CH_2)_n$; n is an integer of 7–11; and the $CH_2$ of X may be replaced by an oxygen atom, a hetero ring, or an aromatic ring, but oxygen atoms are not sequentially arranged in X].

4. An optical resolution agent comprising the β-diketone compound as recited in claim 3.

5. A metal-coordinated β-diketone compound in which a metal is coordinated with the β-diketone compound as recited in claim 2.

6. An organic synthesis method characterized in that a metal is coordinated with a β-diketone compound as recited in claim 2, to thereby form a metal-coordinated β-diketone compound, and the resultant metal-coordinated β-diketone compound is employed as a catalyst for an organic synthesis reaction, an asymmetric synthesis reaction, or an asymmetric recognition reaction.

7. A catalyst for an organic synthesis reaction, an asymmetric synthesis reaction, or an asymmetric recognition reaction, characterized by comprising the metal-coordinated β-diketone compound as recited in claim 5.

* * * * *